United States Patent
Ishii et al.

(10) Patent No.: US 8,772,195 B2
(45) Date of Patent: Jul. 8, 2014

(54) METHOD FOR PRODUCING SILICA-SUPPORTED CATALYST, AND METHOD FOR PRODUCING UNSATURATED CARBOXYLIC ACID OR UNSATURATED NITRILE

(75) Inventors: Yusuke Ishii, Tokyo (JP); Takaaki Kato, Tokyo (JP)

(73) Assignee: Asahi Kasei Chemicals Corporation, Tokyo (JP)

( * ) Notice: Subject to any disclaimer, the term of this patent is extended or adjusted under 35 U.S.C. 154(b) by 184 days.

(21) Appl. No.: 13/146,983

(22) PCT Filed: Jan. 21, 2010

(86) PCT No.: PCT/JP2010/050679
§ 371 (c)(1),
(2), (4) Date: Jul. 29, 2011

(87) PCT Pub. No.: WO2010/087262
PCT Pub. Date: Aug. 5, 2010

(65) Prior Publication Data
US 2011/0288325 A1    Nov. 24, 2011

(30) Foreign Application Priority Data

Jan. 30, 2009 (JP) .................................. 2009-020066

(51) Int. Cl.
*B01J 21/00* (2006.01)
*B01J 23/00* (2006.01)
*B01J 27/25* (2006.01)

(52) U.S. Cl.
USPC ........... 502/246; 502/201; 502/247; 502/248; 502/249; 502/254; 502/255; 502/305; 502/309; 502/311; 502/312; 502/321

(58) Field of Classification Search
USPC ......... 502/246–249, 254, 309, 311, 312, 321, 502/255, 305, 201
See application file for complete search history.

(56) References Cited

U.S. PATENT DOCUMENTS

| | | | |
|---|---|---|---|
| 4,405,498 A | | 9/1983 | Ebner |
| 4,587,226 A | * | 5/1986 | Sasaki et al. .................... 502/5 |
| 4,590,173 A | * | 5/1986 | Sasaki et al. .................. 502/204 |
| 6,037,304 A | | 3/2000 | Abdulwahed et al. |
| 6,143,690 A | | 11/2000 | Komada et al. |
| 6,486,091 B1 | | 11/2002 | Abdulwahed et al. |
| 7,109,144 B2 | | 9/2006 | Hinago et al. |
| 7,645,897 B2 | * | 1/2010 | Tu et al. ........................ 558/319 |
| 7,919,430 B2 | | 4/2011 | Tateno et al. |

FOREIGN PATENT DOCUMENTS

| | | |
|---|---|---|
| CN | 1031822 A | 3/1989 |
| CN | 1097351 A | 1/1995 |
| CN | 1360971 | 7/2002 |
| EP | 0 279 374 | 8/1988 |
| EP | 1 113 238 A2 | 7/2001 |
| JP | 6-316407 | 11/1994 |
| JP | 2001-259420 | 9/2001 |
| JP | 2001-276618 | 10/2001 |
| JP | 2002-219362 | 8/2002 |
| WO | WO 2007/119376 A1 | 10/2007 |

OTHER PUBLICATIONS

European Search Report for EP Application No. 10735731.1 dated Jan. 7, 2013.
International Preliminary Report on Patentability dated Apr. 27, 2010 issued in International Application No. PCT/JP2010/050679.
International Preliminary Report on Patentability dated Aug. 18, 2011 issued in International Application No. PCT/JP2010/050679.
International Search Report from Japanese Patent Office for International Application No. PCT/JP2010/050679, Mailed Apr. 27, 2010.
Office Action for TW Application No. 099102731 mailed Feb. 27, 2013.
Chinese Office Action for CN Application No. 201080005913.2 mailed Nov. 2, 2012.

* cited by examiner

*Primary Examiner* — Cam N. Nguyen
(74) *Attorney, Agent, or Firm* — Finnegan, Henderson, Farabow, Garrett & Dunner, LLP

(57) ABSTRACT

To produce a silica-supported catalyst having an excellent yield of a target product and excellent catalyst attrition resistance.
A method for producing a silica-supported catalyst comprising Mo, V, Nb, and a component X (Sb and/or Te) to be used in a vapor phase catalytic oxidation or ammoxidation of propane, comprising the steps of:
(I) preparing a raw material mixture solution by mixing Mo, V, Nb, component X, a silica sol, and water;
(II) obtaining a dry powder by drying the raw material mixture solution; and
(III) obtaining a silica-supported catalyst by calcining the dry powder, wherein the silica sol contains 10 to 270 wt ppm of nitrate ions based on $SiO_2$.

6 Claims, No Drawings

METHOD FOR PRODUCING SILICA-SUPPORTED CATALYST, AND METHOD FOR PRODUCING UNSATURATED CARBOXYLIC ACID OR UNSATURATED NITRILE

TECHNICAL FIELD

The present invention relates to a method for producing a silica-supported catalyst which is used in a vapor phase catalytic oxidation or ammoxidation of propane.

BACKGROUND ART

It is known that an unsaturated carboxylic acid or an unsaturated nitrile can be synthesized by a vapor phase catalytic oxidation or ammoxidation reaction using an alkane as a starting raw material. As the catalyst for the vapor phase catalytic oxidation or ammoxidation reaction, a composite metal oxide containing Mo, V, and Te, or containing Mo, V, and Nb is used. Since the yield of the target unsaturated carboxylic acid or unsaturated nitrile directly relies on the composition of the composite metal oxide, in the past various compositions have been investigated.

On the other hand, it is also known that the carrier on which the composite metal oxide is supported and the physical properties and chemical properties of the whole catalyst have an effect, though not small, on catalyst performance. Accordingly, investigations are progressing on this point too.

Patent Literature 1 describes, as a catalyst for a vapor phase catalytic oxidation reaction or vapor phase catalytic ammoxidation reaction of propane or isobutane, a catalyst which supports a composite metal oxide containing Mo, V, Nb, and B on silica which has a $SiO_2$ content of 20 to 60 mass % based on the total mass of the oxide and the silica.

Patent Literature 2 describes a silica-supported catalyst which is used when producing an unsaturated nitrile by a vapor phase catalytic ammoxidation reaction of propane or isobutane, or used when producing an unsaturated carboxylic acid by a vapor phase catalytic oxidation reaction. The described silica-supported catalyst has a specific metal component composition, silica content, and pore volume.

CITATION LIST

Patent Literature

[Patent Literature 1] Japanese Patent Laid-Open No. 2001-276618
[Patent Literature 2] Japanese Patent Laid-Open No. 2002-219362

SUMMARY OF INVENTION

Technical Problem

Improvements to catalyst performance which focus on the carrier can be expected to have an effect on catalyst performance as a result of changes to the carrier amount or type, when the catalytic active sites in the crystal structure have formal relatedness. Thus, such improvements are considered to be an effective technique. Accordingly, the present inventors carried out investigations into catalyst performance which focused on a silica sol, which is a carrier, and on various cations and anions to be included in the silica sol. Consequently, although a definite cause-and-effect is not clear, the present inventors discovered that the state of aggregation of the silica sol used as the carrier has some effect on the attrition resistance of the obtained catalyst and on the yield of the catalyst.

Solution to Problem

As a result of continued extensive research based on the above-described perspective, the present inventors discovered that the aggregation state of a silica sol can be appropriately controlled by adjusting the concentration of nitrate ions in the silica sol, which is a silica carrier raw material, in a specific range. Further, the present inventors discovered that by using such a silica sol as a carrier raw material, a good yield can be exhibited in a propane oxidation reaction and ammoxidation reaction, and that a silica-supported catalyst having excellent attrition resistance can be obtained, thereby arriving at the present invention.

Specifically, the present invention is a method for producing a silica-supported catalyst as described below, and a method for producing an unsaturated carboxylic acid or an unsaturated nitrile using this silica-supported catalyst.

[1] A method for producing a silica-supported catalyst comprising Mo, V, Nb, and a component X (Sb and/or Te) to be used in a vapor phase catalytic oxidation or ammoxidation of propane, comprising the steps of:
(I) preparing a raw material mixture solution by mixing Mo, V, Nb, component X, a silica sol, and water;
(II) obtaining a dry powder by drying the raw material mixture solution; and
(III) obtaining a silica-supported catalyst by calcining the dry powder, wherein the silica sol contains 10 to 270 wt ppm of nitrate ions based on $SiO_2$.

[2] The method for producing the silica-supported catalyst according to the above [1], wherein the silica-supported catalyst is represented by the following general composition formula (1), $$Mo_1V_aX_bNb_cZ_dO_n \tag{1}$$

(wherein X represents Sb and/or Te, Z represents at least one element selected from the group consisting of W, Ta, Ti, Mn, B, Bi, Y, and rare earth elements, a, b, c, d, and n represent the atomic ratio of the individual element to the element Mo, a, b, c, and d are $0.01 \leq a \leq 1$, $0.01 \leq b \leq 1$, $0.01 \leq c \leq 0.6$, and $0 \leq d \leq 1$, and respectively, and n represents a number determined based on an oxidation state of component metals).

[3] The method for producing the silica-supported catalyst according to the above [1] or [2], wherein the component X is Sb.

[4] The method for producing the silica-supported catalyst according to the above [2] or [3], wherein the component Z is at least one element selected from the group consisting of W, Mn, and Ce.

[5] The method for producing the silica-supported catalyst according to any of the above [1] to [4], wherein a silica content of the silica-supported catalyst is 35 to 70 mass % based on a total mass of the catalyst.

[6] The method for producing the silica-supported catalyst according to any of the above [1] to [5], wherein the raw material mixture solution further comprises a silica powder.

[7] A method for performing a vapor phase catalytic oxidation of propane to produce a corresponding unsaturated carboxylic acid, comprising the step of: introducing propane into a reaction vessel containing a silica-supported catalyst produced by the method according to any of the above [1] to [6].

[8] A method for performing a vapor phase catalytic ammoxidation of propane to produce a corresponding unsaturated nitrile, comprising the step of: introducing propane and ammonia into a reaction vessel containing a silica-supported catalyst produced by the method according to any of the above [1] to [6].

Advantageous Effects of Invention

A silica-supported catalyst produced by the production method according to the present invention has an excellent target product yield and excellent catalyst attrition resistance.

DESCRIPTION OF EMBODIMENTS

A mode for carrying out the present invention (hereinafter, referred to as "present embodiment") will now be described in more detail. However, the present invention is not limited to the present embodiment. The present invention may be carried out while making various modifications within the scope of the invention.

[1] Method for Producing Silica-Supported Catalyst

A method for producing a silica-supported catalyst according to the present embodiment comprising Mo, V, Nb, and a component X (Sb and/or Te) to be used in a vapor phase catalytic oxidation or ammoxidation of propane, comprising the steps of:

(I) preparing a raw material mixture solution by mixing Mo, V, Nb, component X, a silica sol, and water;
(II) obtaining a dry powder by drying the raw material mixture solution; and
(III) obtaining a silica-supported catalyst by calcining the dry powder, wherein the silica sol contains 10 to 270 wt ppm of nitrate ions based on $SiO_2$.

As a result of extensive investigations focused on the content of the slight amount of nitrate ions included in a silica sol used as a carrier raw material, the present inventors discovered that a catalyst can be produced which has excellent attrition resistance and an excellent target product yield by preparing the catalyst using a silica sol having a nitrate ion content of 10 to 270 wt ppm based on the $SiO_2$ (silica) in the silica sol. At this stage, it is not the amount of nitrate ions present in the whole raw material mixture solution (slurry) that is important, rather it is the amount of nitrate ions based on the $SiO_2$ in the silica sol which is added to the slurry that is important. A catalyst having excellent attrition resistance can maintain an initial yield for a long period of time.

If the nitrate ion content based on the silica in the silica sol is less than 10 wt ppm, the attrition resistance of the obtained catalyst deteriorates. The present inventors presume that the reason for this deterioration is due to the difficulty of the sintering among the silica sol primary particles to progress during the below-described calcination step to obtain the catalyst. On the other hand, if the nitrate ion content is more than 270 wt ppm, the yield of the target product decreases. Although the reason for this is unclear, the present inventors presume that this is because the binding between the metal species and the nitrate ions causes some kind of adverse impact on the production of the catalytic active species, which results in a decrease in the amount of the catalytic active species.

Until now, investigations have been carried out on cationic species regarding the effect of impurities in the silica sol used in the carrier. Among cationic species, since metal species such as alkali metals and alkaline earth metals represented by sodium, potassium, and magnesium, remain in the obtained silica-supported catalyst, it is thought that such metal species have an effect on the performance of the catalyst. More specifically, attention has been paid to cationic species due to the fact that depending on the kind of the cationic species, the effect on the catalyst is large. In contrast, the fact that the presence of nitrate ions, which are an anionic species, in the raw material mixture solution can have an effect on the performance of the silica-supported catalyst has not been investigated until now. Thus, this is a new focus point.

The concentration of nitrate ions based on the silica in the silica sol can be calculated by ion chromatography. The measurement apparatus and the measurement conditions are shown below. As the measurement apparatus, the IC-2001 manufactured by Tosoh Corporation can be used. The TSKgel superIC-AZ is used as a column. The TSKguardcolumn superIC-AZ is used as a guard column. Further, TSKsupress A is used as a suppress valve washing solution, and a mixture of a 1.9 mmol/L $NaHCO_3$ aqueous solution and a 3.2 mmol/L $Na_2CO_3$ aqueous solution is used as an eluent. The flow rate at this stage is 0.8 mL/min.

The silica sol used as a raw material for the silica carrier contains 10 to 270 wt ppm, and more preferably 10 to 200 wt ppm, of nitrate ions based on the $SiO_2$ in the silica sol. In the present specification, the term "silica sol" refers to a transparent aqueous solution of silicic acid. From the perspective of improving the strength of the catalyst, the content of the carrier silica in the catalyst is preferably 35 mass % or more based on the total mass ratio of the silica-supported catalyst formed from a catalyst component and silica. From the perspective of conferring sufficient activity, this content is preferably 70 mass % or less, and more preferably 40 to 65 mass % based on the total mass ratio.

Examples of industrial production methods of silica sols include: (1) dialysis after water glass neutralization; (2) electrodialysis; (3) dissolution of metal silicon in ammonia or an aqueous amine solution; (4) deflocculation of a silica gel; and (5) removal of sodium from water glass using an ion-exchange resin. Among these methods, the most common silica sol production method is a method using an ion-exchange resin. To increase stability under high concentrations, a stabilizing agent such as LiOH, NaOH, and KOH is added to silica sols produced by an ion-exchange resin method. Therefore, the stable pH range of a silica sol is typically about 8 to 10. For a silica sol to maintain a stable dispersion state, the silica particles in the sol have to electrostatically repel each other. Thus, gelation is prevented by, as described above, adding a stabilizing agent so that $OH^-$ groups are adsorbed on the surface of the silica particles to exhibit a stabilization effect due to the negative charge. However, it is known that if too much alkali (alkali metal ions in the stabilizing agent) is added, the alkali ions adsorb, which results in the negative charge decreasing, and the silica sol becoming unstable. Recently, many silica sols having these inherent characteristics of such silica sols which can be used in various applications are commercially available. Examples include, in the Snowtex series from Nissan Chemical Industries, Ltd., Snowtex 30 having a 30% silica sol concentration, Snowtex C used in application for which there is a risk of gelation occurring, Snowtex N which aims to eliminate the risk of residual alkali component by using a volatile weak base as a stabilizing agent, and Snowtex O which is suited for applications that require use under acidic conditions (Reference Document: Catalyst Engineering Course 10, By Element, Catalyst Handbook, pub. Feb. 25, 1967).

Focusing on the surface of the silica particles of the silica sol obtained by the above-described production method, such surfaces can be classified into acidic types and alkali types. However, nitrate ions are scarcely present in a silica sol for either type. For example, for an acidic type, hydrogen ions are mainly used as the stabilizing agent. On the other hand, for an alkali type, sodium ions or ammonium ions are used as the stabilizing agent. As the counteranion for an acidic type, $SO_4^{2-}$, $Cl^-$ and the like are used. As the counteranion for an alkali type, OFF is typically used.

In the production method according to the present embodiment, for either the above-described acidic type or alkali type of silica sol, to obtain a silica sol having a nitrate ion mass ratio of 10 to 270 wt ppm based on the mass of silica, it is preferred to add nitric acid or a nitric acid salt such as ammonium nitrate during the neutralization of the water glass aqueous solution with sulfuric acid or hydrochloric acid, which is a typical silica sol production method, to adjust the nitrate ion content based on silica to 10 to 270 wt ppm. Further, after neutralizing with sulfuric acid or hydrochloric acid, the nitrate ions may be exchanged with the anion in the water glass aqueous solution by ion exchange. Alternatively, the nitrate ion content may be adjusted by adding nitrate ions into the existing silica sol with a dropper and the like. Other than nitric acid, the nitric acid source may be a salt such as ammonium nitrate or the like.

Examples of the method for preparing the silica sol containing nitrate ions in a specific range which is used as a carrier raw material for the silica-supported catalyst according to the present embodiment will now be described in more detail.

An example of the method for preparing the silica sol which may be used is to:
(a) To an aqueous solution of a silicic acid salt such as water glass,
(b) add a non-polar liquid medium (toluene, xylene, kerosene etc.) containing a surfactant (nonionic surfactants such as polyethylene glycol fatty acid ester, polyoxyethylene alkyl phenyl ether, polyoxyethylene alkyl ether, sorbitan fatty acid ester, polyoxyethylene sorbitan fatty acid monoester etc.), and
(c) stir to obtain a sol-like product (refer to Japanese Patent Examined Publication No. 02-020563).

In this case, so that the nitrate ion content based on the silica in the obtained silica sol is 10 to 270 wt ppm, nitric acid may be added to the aqueous solution of silicic acid and/or the surfactant solution. Further, the nitric acid may be added during or after the stirring step.

Further, another method that can be used is to add, to a reaction medium containing an alkali and water, an alkyl silicate in an amount so that the resultant mixture contains 7 to 80 moles of Si atoms based on 1 mole of the alkali, and hydrolyze the alkyl silicate at 45° C. to a temperature at or below the boiling point of the reaction medium (refer to Japanese Patent Laid-Open No. 06-316407). In this case, as long as the hydrolysis reaction is not hindered, the nitric acid may be added before hydrolysis. However, generally, it is preferred to add the nitric acid after the hydrolysis step, so that the nitrate ion content is 10 to 270 wt ppm based on the obtained silica.

A further example is to obtain a silica sol by mixing industrial sodium water glass ($SiO_2$/$Na_2O$ molar ratio, 3 to 4) with water to prepare an aqueous solution of sodium silicate, mix this aqueous solution of sodium silicate with a solution of silicic acid in an aqueous colloid ($SiO_2$ concentration, 1 to 10 mass %; pH, 1.5 to 3.5), and heat and stir the resultant mixture for about 0.1 to 10 hours at 40 to 60° C. (refer to Japanese Patent Laid-Open No. 62-7622). Here, it is preferred to prepare the aqueous solution of sodium silicate in a reaction vessel which is equipped with a stirring device, a condenser, and a dropping funnel, and add the solution of silicic acid in an aqueous colloid so that the resultant mixture can be immediately heated and stirred. The solution of silicic acid in an aqueous colloid can be prepared by treating a dilute aqueous solution of sodium silicate with a hydrogen cation exchange resin. The nitric acid may be charged into the aqueous solution of sodium silicate so that the resultant mixture has a desired concentration based on the silica in the obtained silica sol. After the heating and stirring step, the mixture may optionally be aged (e.g., 0.5 to 5 hours, 40 to 70° C.), to produce a silica sol having a pH of about 8 to 11.

When producing a strongly acidic silica sol, a method can be used in which a water glass aqueous solution is pressure fed, and a mineral acid such as sulfuric acid is sprayed under pressure into the water glass aqueous solution (refer to Japanese Patent Examined Publication No. 05-075692). In this production method, nitric acid may be added to the water glass aqueous solution, or a mixture of nitric acid and sulfuric acid may be sprayed into the water glass aqueous solution.

The silica carrier raw material can be a silica sol only, or a part can be replaced with a silica powder. By using a silica powder for the silica carrier raw material, effects such as an improvement of catalytic activity and/or target product yield can be expected. However, if the catalyst is prepared without using a silica sol, and only using a silica powder, the attrition resistance of the catalyst markedly deteriorates. In the present specification, the term "silica powder" refers to fine particles of solid $SiO_2$. If the primary particle size of the silica is too large, the obtained tends to be brittle. Therefore, a nanometer size silica powder is preferred. The silica powder is preferably produced by a high-heat method. Specific examples of preferred silica powders include Aerosil 200 manufactured by Nippon Aerosil Co., Ltd.

When using a silica sol with silica powder as the silica carrier raw material, the silica powder is preferably 20 to 80 mass % of the total content of the silica sol and the silica powder. If the silica powder content is 20 mass % or more, the yield of the target product tends to improve. If the silica powder content is 80 mass % or less, the attrition resistance of the catalyst tends to improve. Further, the silica powder does not have to contain nitrate ions. As long as the nitrate ion concentration in the silica sol is 10 to 270 wt ppm based on $SiO_2$, this is within the scope of the present invention.

The three steps according to the present embodiment, step (I) of preparing a raw material mixture solution, step (II) of obtaining a dry powder by drying the raw material mixture solution obtained in step (I), and step (III) of calcining the dry powder obtained in step (II), will now be described.

Step (I): Step of Preparing a Raw Material Mixture Solution

Step (I) is a step of preparing a raw material mixture solution by mixing Mo, V, Nb, component X, a silica sol, and water. In this step, the raw materials of the catalyst-constituting elements are dissolved or dispersed in a solvent. The raw material mixture solution is a solution or a slurry containing all of the catalyst-constituting metals and carrier components.

Examples of the raw materials which may be used as the component metals of the silica-supported catalyst include, but are not limited to, the following compounds.

Examples of Mo raw materials include molybdic acid, molybdenum oxides, molybdenum oxychlorides, molybdenum chlorides, molybdenum alkoxides, ammonium heptamolybdate and the like. Of these, it is preferred to use ammonium heptamolybdate.

Examples of V raw materials include ammonium metavanadate, vanadium (V) oxide, vanadium oxychlorides, and vanadium alkoxides. Of these, it is preferred to use ammonium metavanadate.

Examples of Nb raw materials which can be used include at least one from niobic acid, an inorganic salt of niobium, and an organic salt of niobium. Of these, it is preferred to use niobic acid. Niobic acid is represented by $Nb_2O_5 \cdot nH_2O$, and is also called niobium hydroxide or niobium oxide hydrate. In actual practice, when used as a catalyst, the niobium raw material is used as a niobium raw material solution (A) which is dissolved in aqueous oxalic acid. Oxalic acid and/or aqueous hydrogen peroxide can be added to at least a part of this niobium raw material solution (A). In this case, the $H_2O_2/Nb$ molar ratio is preferably 1 to 20, and the oxalic acid/Nb molar ratio is preferably 1 to 4.

Examples of Sb raw materials include antimony oxides. Of these, it is preferred to use antimony(III) oxide.

Examples of Te raw materials include telluric acid and metal tellurium. Of these, it is preferred to use telluric acid.

Step (I) of preparing a raw material mixture solution will be described using an example in which a silica-supported catalyst containing molybdenum, vanadium, niobium, and antimony is produced.

First, ammonium heptamolybdate, ammonium metavanadate and antimony(III) oxide are charged into water, and the resultant mixture is heated to prepare a raw material solution (B). At this stage, the interior of the vessel may be a nitrogen or an argon atmosphere. This raw material solution (B), the above-described niobium raw material solution (A), and a silica sol are mixed in a preferred ratio to obtain the raw material mixture solution. When the silica carrier raw materials include a silica powder, it is preferred to use the silica powder after dispersing it in water. The dispersion of silica powder in water may be added to the mixed solution of the raw material solution (B) and the niobium raw material solution (A) after mixing with the silica sol, or may be directly added to the mixed solution of the raw material solution (B) and the niobium raw material solution (A). Usually, the raw material mixture solution is in the form of a slurry. It is preferred to add hydrogen peroxide to this raw material mixture solution, or to a liquid containing the components of the mixed solution midway through preparation of the raw material mixture solution. At this stage, the $H_2O_2/Sb$ (molar ratio) is preferably 0.01 to 10, and more preferably 0.5 to 4. It is preferred to continue stirring for 30 minutes to 2 hours at 30 to 70° C.

Step (II): Drying Step

Step (II) is a step of obtaining a dry powder by drying the raw material mixture solution obtained in step (I). The drying can be carried out by a spray drying method, an evaporation drying method and the like. The atomization in the spray drying method can be conducted by centrifugation, a two-fluid nozzle method, or by a high-pressure nozzle method. As the heat source for the drying, air heated by steam, an electric heater and the like may be used. The hot-air dryer inlet temperature is preferably 150 to 300° C. The obtained dry powder is preferably quickly supplied to the following calcination step (III). If there is a need to store the dry powder, the dry powder is preferably stored in a dry atmosphere so that it does not absorb moisture.

Step (III): Calcination Step

Step (III) is a step of obtaining a silica-supported catalyst by calcining the dry powder obtained in step (II). The calcination may be carried out using a rotary furnace, a tunnel furnace, a ring furnace, a fluidized calcination furnace, a rotary kiln and the like. If the dry powder is left to stand and then calcined, the dry powder is not uniformly calcined, and performance deteriorates. Further, this also causes the occurrence of adherence, cracks, and fissures of the catalyst components in the furnace. Thus, considering productivity as an industrial catalyst, it is preferred to carry out this step using a fluidized calcination furnace or a rotary kiln.

If the oxidation number of the metal elements constituting the silica-supported catalyst have an effect of catalyst performance, the calcination is preferably carried out under nitrogen or similar gas atmosphere which is essentially free from oxygen. More preferably, the calcination is carried out while flowing an inert gas. The flow rate of the inert gas is, based on 1 kg/hr of dry powder, preferably 0.05 to 20 Nm³/Hr, and more preferably 0.1 to 12 Nm³/Hr. For continuous flow calcination using a rotary kiln, the flow rate of the inert gas is, based on 1 kg/Hr of dry powder, preferably 0.05 to 20 Nm³/Hr, and more preferably 0.1 to 12 Nm³/Hr.

A silica-supported catalyst obtained by the production method according to the present embodiment preferably has a composition represented by the following general composition formula (1),

$$Mo_1V_aX_bNb_cZ_dO_n \qquad (1)$$

(wherein X represents Sb and/or Te, Z represents at least one element selected from the group consisting of W, Ta, Ti, Mn, B, Bi, Y, and rare earth elements, a, b, c, d, and n represent an atomic ratio of the individual element to the element Mo, a, b, c, and d are $0.1 \leq a \leq 1$, $0.01 \leq b \leq 1$, $0.01 \leq c \leq 0.6$, and $0 \leq d \leq 1$, and respectively, and n represents a number determined based on an oxidation state of component metals).

Although the reason is not clear, if the catalyst contains W, Mn, or Ce, when the catalyst is used in an oxidation or ammoxidation reaction, the yield tends to improve. Therefore, component Z is preferably at least one selected from the group consisting of W, Mn, and Ce.

a, b, c, and d are respectively $0.1 \leq a \leq 1$, $0.01 \leq b \leq 1$, $0.01 \leq c \leq 0.6$, and $0 \leq d \leq 1$, and preferably $0.15 \leq a \leq 0.5$, $0.10 \leq b \leq 0.5$, $0.02 \leq c \leq 0.3$, and $0 \leq d \leq 0.3$. If a, b, c, and d are in this range, degradation of the target product can be prevented. Further, since the produced amount of reaction by-products is suppressed, the target product tends to be obtained in a better yield.

The silica-supported catalyst represented by the above composition formula (1) is preferable from the perspective that the yield in a propane vapor phase catalytic oxidation reaction or a propane vapor phase catalytic ammoxidation reaction is good. The effect of an improvement in attrition resistance of the catalyst due to using a specific silica sol as a silica carrier raw material is not limited to being exhibited in catalysts represented by the above composition formula (1).

[2] Method for Producing the Unsaturated Carboxylic Acid or Unsaturated Nitrile

The method for producing the unsaturated carboxylic acid according to the present embodiment is a method for producing a corresponding unsaturated carboxylic acid by introducing propane into a reaction vessel containing a silica-supported catalyst produced by the production method according to the present embodiment, and performing a vapor phase catalytic oxidation reaction.

Further, the method for producing the unsaturated nitrile according to the present embodiment is a method for producing a corresponding unsaturated nitrile by introducing propane and ammonia into a reaction vessel containing a silica-supported catalyst produced by the production method according to the present embodiment, and performing a vapor phase catalytic ammoxidation reaction.

In the method for producing the unsaturated carboxylic acid or unsaturated nitrile according to the present embodiment, a vapor phase catalytic oxidation reaction or a vapor phase catalytic ammoxidation reaction proceeds by introducing propane or propane and ammonia, and oxygen, which are the raw materials, into a reaction vessel which already contains a silica-supported catalyst, and setting to a predetermined temperature. It is preferred to select an appropriate catalyst based on the reaction method. Since the catalyst according to the present embodiment is quite strong, this catalyst has sufficient resistance even as a catalyst for a fluidized-bed reaction. However, the catalyst according to the present embodiment can obviously also be used as a catalyst for a fixed-bed reaction. The supplied raw materials for the propane and the ammonia do not have to be of a high purity. Industrial grade gases may be used for these raw materials. As the supplied oxygen source, air, pure oxygen, or air enriched with pure oxygen may be used. Further, a diluting gas such as helium, neon, argon, carbon dioxide gas, steam, nitrogen or the like may also be supplied.

A conventional reaction method such as a fixed-bed, fluidized-bed, or moving-bed method may be used as the reaction method. However, a fluidized-bed reaction is especially preferable, for reasons such as heat removal is simple, the temperature of the catalyst layer can be generally uniformly maintained, and the catalyst can be taken out of and added into the reaction vessel during operation.

The raw material supply rate and reaction temperature may be appropriately set based on the reaction method, the catalytic tendencies and the like. For example, for vapor phase catalytic oxidation, the reaction temperature is usually set at 200 to 400° C. For a vapor phase catalytic ammoxidation reaction, the reaction temperature is usually set at 350 to 500° C.

The method for producing the unsaturated carboxylic acid or unsaturated nitrile may be a single flow method. However, depending on the catalyst, the conversion rate of the raw materials is not always sufficiently high. Thus, from the perspective of effective utilization of the raw materials, unreacted materials among the propane (or propane and ammonia) fed to the reaction vessel may be recovered and re-fed (recycled) into the reaction vessel.

EXAMPLES

The present embodiment will now be described using a production example of the catalyst and a production example of acrylonitrile by a vapor phase catalytic ammoxidation reaction of propane. However, the present embodiment is not limited to these examples.

The results of the ammoxidation reaction were evaluated based on the acrylonitrile (AN) yield (%). As shown by the following formula, the acrylonitrile yield (%) represents the number of moles of the produced acrylonitrile as a percentage based on the number of moles of fed propane.

Acrylonitrile yield(%)=(number of moles of produced acrylonitrile/number of moles of fed propane)×100

The degree of attrition of each catalyst was measured as follows.

About 50 g of catalyst was weighed and charged into a perpendicular tube having an inner diameter of 1.5 inches and a length of 27.5 mm which was equipped with a perforated disk having 3 orifices with an inner diameter of 0.016 inches on the bottom. A pipe (thickness 2 mm, outer diameter 5 inches, length 22 inches, having an aperture with an inner diameter of 1.2 inches on an upper edge portion, whose diameter gradually decreases to an outer diameter of 1.5 inches at a lower edge portion, and which is engaged to an upper edge of the tube) was connected onto the tube. Air was flowed from the bottom for 20 hours at the speed of sound through the hole portions of the perforated disk to cause the catalyst to flow. The catalyst degree of attrition was defined by the following formula.

Degree of attrition(%)=(Catalyst mass which dissipated out of the system from the 5 inch pipe upper portion during 5 hour to 20 hour period)/ ((Initial charge)−(Catalyst mass which dissipated out of the system from the 5 inch pipe upper portion during 0 hour to 5 hour period))×100

The nitrate ion content based on the silica in the silica sol was measured by subjecting the sol to centrifugal separation for 1.5 hours at 15,000 rpm, diluting the supernatant by ½ (v/v) with an eluent, filtering the resultant mixture with a 0.2 µm membrane filter, and then using ion chromatography under the same conditions as described above.

Example 1

A silica-supported catalyst represented by a charge composition formula of $Mo_1V_{0.25}Sb_{0.26}Nb_{0.08}O_n/40$ mass %-$SiO_2$ was produced as follows. It was confirmed that the composition of the catalyst obtained in each of the examples had the same charge composition formula.

Preparation of Niobium Raw Material Solution

A niobium raw material solution was prepared as follows.

A mixture was obtained by charging 250.7 g of niobic acid containing 80.5 mass % as $Nb_2O_5$ and 1,009.1 g of oxalic dihydrate [$H_2C_2O_4.2H_2O$] into 1,740 g of water. The molar ratio of the charged oxalic acid/niobium was 5.0, and the concentration of the charged niobium was 0.510 (mol-Nb/Kg-solution).

This solution was heated and stirred for 1 hour at 95° C. to obtain an aqueous solution in which niobium was dissolved. The aqueous solution was left to stand, cooled with ice, and then the solid matter was separated by suction filtration to obtain a uniform oxalic acid/niobium mixed solution.

10 g of the oxalic acid/niobium mixed solution was weighed into a crucible, and dried overnight at 90° C. The resultant product was then heat treated for 1 hour at 500° C. to obtain 0.885 g of $Nb_2O_5$. From this result, the niobium concentration in the oxalic acid/niobium mixed solution was 0.66 (mol-Nb/Kg-solution), and the oxalic acid/niobium molar ratio was 2.4.

Next, 2.69 g of the oxalic acid/niobium mixed solution was weighed into a 300 mL glass beaker. The glass beaker was charged with 200 mL of approximately 80° C. hot water, and then charged with 10 mL of 50 vol % sulfuric acid to obtain a niobium raw material solution. While maintaining the solution temperature at 70° C. with a hot stirrer, the obtained niobium raw material solution was titrated using ¼ N $KMnO_4$ under stirring. The end point was set at the point where a faint pale peach color due to the $KMnO_4$ continued for about 30 seconds or more. The oxalic acid concentration in the niobium raw material solution was calculated based on the following formula from the titration amount to be 1.53 (mol-oxalic acid/Kg).

The obtained niobium raw material solution was used as niobium raw material solution ($A_0$) in the following catalyst preparation.

Raw Material Mixture Solution Preparation Step

A mixed solution ($C_1$) was prepared by charging 1,237.4 g of ammonium heptamolybdate [$(NH_4)_6Mo_7O_{24}.4H_2O$], 203.6 g of ammonium metavanadate [$NH_4VO_3$], and 265.0 g of antimony trioxide [$Sb_2O_3$] into 6,500 g of water, and heating the resultant mixture for 1 hour at 90° C. while stirring.

200.5 g of hydrogen peroxide solution containing 30 mass % as $H_2O_2$ was slowly charged into 940.4 g of the niobium raw material solution ($A_0$) while stirring under ice cooling. The resultant solution was then stirred and mixed to obtain a mixed solution ($A_1$).

Further, 260 g of silica powder having an average primary particle size of 12 nm was charged into 3,500 g of water, and the resultant mixture was stirred for 3 hours at room temperature to obtain a silica powder suspension (D).

A silica sol, which is the carrier raw material, was prepared according to Example 6 of Japanese Patent Laid-Open No. 6-316407. More specifically, a 3 L stainless steel reaction vessel equipped with a stirring device was charged with 1,775 g of pure water and 11 g of ammonia water. While keeping the system inside the reaction vessel at 80° C. with an oil bath, and stirring the aqueous solution in the reaction vessel, 214 g of tetraethyl silicate was continuously added over 1.4 hours. The temperature of the obtained aqueous suspension was increased to 88° C., and reflux was carried out for 1 hour. Then, the solution was concentrated by evaporating off the liquid in the vessel and externally discharging the vapor until the temperature reached 95° C. The solution was then transferred to a rotary evaporator, and concentrated. The obtained sol had an $SiO_2$ concentration of 29.6 mass %. Nitric acid was added to the silica sol with a dropper until the content of the nitrate ions in the silica sol was 3 ppm. The content of the nitrate ions in this silica sol was 10 wt ppm based on the $SiO_2$ in the silica sol.

The obtained mixed solution ($C_1$) was cooled to 70° C., and then 2,177.8 g of the above-described silica sol was added thereto. Further, 200.5 g of hydrogen peroxide solution containing 30 mass % as $H_2O_2$ was added, and the resultant mixture was stirred and mixed for 30 minutes at 50° C. Next, the mixed solution ($A_1$) and the above silica powder suspension (D) were added. The resultant mixture was stirred and mixed for 3 hours to obtain a raw material mixture solution.

Drying Step

The obtained raw material mixture solution was fed into a centrifugation type spray-dryer to dry, whereby dry microspherical powder was obtained. The inlet temperature of the dryer was 210° C., and the outlet temperature was 120° C.

Calcination Step 350 g of the obtained dry powder was charged into an SUS calcination tube with a 3-inch diameter. Then, under a 2.0 $Nm^3$/HR nitrogen gas flow, the powder was calcined for 5 hours at 700° C. while rotating the tube to obtain the target silica-supported catalyst.

Propane Ammoxidation Reaction 15 g of the obtained catalyst was charged into a Vycor glass fluidized-bed reaction tube having an inner diameter of 15 mm. A mixed gas having a molar ratio of propane:ammonia:oxygen:helium of 1:1:3:15 was fed into the reaction tube at a reaction temperature of 440° C. and a reaction pressure of $1.0 \times 10^5$ Pa. The acrylonitrile yield 3 hours after the start of the reaction is shown in Table 1. Further, the degree of attrition of the obtained catalyst was measured to be 0.6 mass %.

Example 2

A silica-supported catalyst represented by a charge composition formula of $Mo_1V_{0.25}Sb_{0.26}Nb_{0.08}Ce_{0.002}O_n/40$ mass %-$SiO_2$ was produced as follows.

Preparation of Niobium Raw Material Solution

A niobium raw material solution was prepared according to the same method as in Example 1.

Raw Material Mixture Solution Preparation Step

A mixed solution ($C_1$) was prepared by charging 1,237.4 g of ammonium heptamolybdate [$(NH_4)_6Mo_7O_{24}.4H_2O$], 203.6 g of ammonium metavanadate [$NH_4VO_3$], 265.0 g of antimony trioxide [$Sb_2O_3$] and 6.2 g of cerium(III) nitrate hexahydrate [$Ce(NO_3)_3.6H_2O$] into 6,500 g of water, and heating the resultant mixture for 1 hour at 90° C. while stirring.

200.5 g of hydrogen peroxide solution containing 30 mass % as $H_2O_2$ was slowly charged into 940.4 g of the niobium raw material solution ($A_0$) while stirring under ice cooling. The resultant solution was then stirred and mixed to obtain a mixed solution ($A_1$).

Further, 260 g of silica powder having an average primary particle size of 12 nm was charged into 3,500 g of water, and the resultant mixture was stirred for 3 hours at room temperature to obtain a silica powder suspension (D).

A silica sol, which is the carrier raw material, was prepared according to Example 6 of Japanese Patent Laid-Open No. 6-316407. More specifically, a 3 L stainless steel reaction vessel equipped with a stirring device was charged with 1,775 g of pure water and 11 g of ammonia water. While keeping the system inside the reaction vessel at 80° C. with an oil bath, and stirring the aqueous solution in the reaction vessel, 214 g of tetraethyl silicate was continuously added over 1.4 hours. The temperature of the obtained aqueous suspension was increased to 88° C., and reflux was carried out for 1 hour. Then, the solution was concentrated by evaporating off the liquid in the vessel and externally discharging the vapor until the temperature reached 95° C. The solution was then transferred to a rotary evaporator, and concentrated. The obtained sol had an $SiO_2$ concentration of 29.6 mass %. Nitric acid was added to the silica sol with a dropper until the content of the nitrate ions in the silica sol was 3 ppm. The content of the nitrate ions in this silica sol was 10 wt ppm based on the $SiO_2$ in the silica sol.

The obtained mixed solution ($C_1$) was cooled to 70° C., and then 2,177.8 g of the above-described silica sol was added thereto. Consequently, the total mass of all the nitrate ions based on the $SiO_2$ derived from the silica sol in the obtained slurry was 4,137 wt ppm. Further, 240.2 g of hydrogen peroxide solution containing 30 mass % as $H_2O_2$ was added, and the resultant mixture was stirred and mixed for 30 minutes at 50° C. Next, the mixed solution ($A_1$) and the above silica powder suspension (D) were added. The resultant mixture was stirred and mixed for 3 hours to obtain a raw material mixture solution.

Drying Step and Calcination Step

A silica-supported catalyst was obtained by carrying out a drying step and a calcination step in the same manner as in Example 1, except that the raw material mixture solution obtained in the above raw material mixture solution preparation step was used.

Propane Ammoxidation Reaction 15 g of the obtained catalyst was charged into a Vycor glass fluidized-bed reaction tube having an inner diameter of 15 mm. A mixed gas having a molar ratio of propane:ammonia:oxygen:helium of 1:1:3:15 was fed into the reaction tube at a reaction temperature of 440° C. and a reaction pressure of $1.0 \times 10^5$ Pa. The acrylonitrile yield 3 hours after the start of the reaction is shown in Table 1. Further, the degree of attrition of the obtained catalyst was measured to be 0.4 mass %.

Example 3

A catalyst was prepared according to the same method as in Example 2, except that in the raw material mixture solution preparation step, nitric acid was added so that the nitrate ion content of the silica sol ($SiO_2$ concentration, 29.6 mass %) was 10 wt ppm. In addition, the mass of the nitrate ions in the silica sol with respect to the $SiO_2$ mass in the silica sol was 34 wt ppm. Consequently, the total mass of all the nitrate ions based on the $SiO_2$ derived from the silica sol in the obtained slurry was 4,160 wt ppm.

Using the obtained catalyst, a propane ammoxidation reaction and measurement of the degree of attrition of the catalyst were carried out according to the same method as in Example 1. The results are shown in Table 1.

Example 4

A catalyst was prepared according to the same method as in Example 2, except that in the raw material mixture solution preparation step: nitric acid was added so that the nitrate ion concentration in the silica sol ($SiO_2$ concentration, 29.6 mass %) was 10 wt ppm; and cerium(III) carbonate [$Ce_2(CO_3)_3$] was used as the cerium raw material. The mass of the nitrate ions in the silica sol with respect to the $SiO_2$ mass in the silica sol was 34 wt ppm. Consequently, the total mass of all the nitrate ions based on the $SiO_2$ derived from the silica sol in the obtained slurry was 34 wt ppm.

Using the obtained catalyst, a propane ammoxidation reaction and measurement of the degree of attrition of the catalyst were carried out according to the same method as in Example 1. The results are shown in Table 1.

Example 5

A catalyst was prepared according to the same method as in Example 2, except that in the raw material mixture solution preparation step, nitric acid was added so that the concentration in the silica sol, in which the $SiO_2$ concentration was 29.6 mass %, was 30 wt ppm. In addition, the mass of the nitrate ions in the silica sol with respect to the $SiO_2$ mass was 101 wt ppm. Consequently, the total mass of all the nitrate ions based on the $SiO_2$ derived from the silica sol in the obtained slurry was 4,228 wt ppm.

Using the obtained catalyst, a propane ammoxidation reaction and measurement of the degree of attrition of the catalyst were carried out according to the same method as in Example 1. The results are shown in Table 1.

Example 6

A catalyst was prepared according to the same method as in Example 2, except that in the raw material mixture solution preparation step, a silica sol containing 29.6 mass % of $SiO_2$ and 59 wt ppm of nitrate ions in the silica sol (prepared in the same manner as in Example 1) was used. In addition, the mass of the nitrate ions in the silica sol with respect to the $SiO_2$ mass was 199 wt ppm. Consequently, the total mass of all the nitrate ions based on the $SiO_2$ derived from the silica sol in the obtained slurry was 4,326 wt ppm.

Using the obtained catalyst, a propane ammoxidation reaction and measurement of the degree of attrition of the catalyst were carried out according to the same method as in Example 1. The results are shown in Table 1.

Example 7

A catalyst was prepared according to the same method as in Example 2, except that in the raw material mixture solution preparation step, a silica sol containing 29.6 mass % of $SiO_2$ and 79 wt ppm of nitrate ions in the silica sol (prepared in the same manner as in Example 1) was used. In addition, the mass of the nitrate ions in the silica sol with respect to the $SiO_2$ mass was 267 wt ppm. Consequently, the total mass of all the nitrate ions based on the $SiO_2$ derived from the silica sol in the obtained slurry was 4,393 wt ppm.

Using the obtained catalyst, a propane ammoxidation reaction and measurement of the degree of attrition of the catalyst were carried out according to the same method as in Example 1. The results are shown in Table 1.

Example 8

A silica-supported catalyst represented by a charge composition formula of $Mo_1V_{0.25}Sb_{0.26}Nb_{0.08}Ce_{0.002}O_n/55$ mass %-$SiO_2$ was prepared as follows.

A mixed solution (E) was obtained by charging 928.1 g of ammonium heptamolybdate [$(NH_4)_6Mo_7O_{24} \cdot 4H_2O$], 152.7 g of ammonium metavanadate [$NH_4VO_3$], 198.8 g of antimony trioxide [$Sb_2O_3$] and 4.6 g of cerium(III) nitrate hexahydrate [$Ce(NO_3)_3 \cdot 6H_2O$] into 4,800 g of water, and heating the resultant mixture for 1 hour at 90° C. while stirring.

200.5 g of hydrogen peroxide solution containing 30 mass % as $H_2O_2$ was slowly charged into 705.4 g of the niobium mixed solution ($A_0$) while stirring under ice cooling. The resultant solution was then stirred and mixed to obtain a mixed solution (F).

Further, 357.7 g of silica powder having an average primary particle size of 12 nm was charged into 4,800 g of water, and the resultant mixture was stirred for 3 hours at room temperature to obtain a silica powder suspension (G).

The mixed solution (E) was cooled to 70° C., and then 2,994.4 g of the silica sol solution was added thereto. This silica sol solution was prepared in the same manner as in Example 1, and contained 40.7 mass % of $SiO_2$ and 10 wt ppm of nitrate ions in the silica sol. The nitrate ions in the silica sol were 25 wt ppm based on the $SiO_2$ in the silica sol. Consequently, the total mass of all the nitrate ions based on the $SiO_2$ derived from the silica sol in the slurry was 2,207 wt ppm. Further, 240.2 g of hydrogen peroxide solution containing 30 mass % as $H_2O_2$ was added, and the resultant mixture was stirred and mixed for 30 minutes at 50° C. Next, the mixed solution (F) and the above silica powder suspension (G) were added. The resultant mixture was stirred and mixed for 3 hours to obtain a raw material mixture solution.

Using the obtained raw material mixture solution, a silica-supported catalyst was obtained by carrying out a drying step and a calcination step in the same method as in Example 1.

Using the obtained catalyst, a propane ammoxidation reaction and measurement of the degree of attrition of the catalyst were carried out according to the same method as in Example 1. The results are shown in Table 1.

Example 9

A silica-supported catalyst represented by a charge composition formula of $Mo_1V_{0.25}Sb_{0.26}Nb_{0.08}Ce_{0.002}O_n/60$ mass %-$SiO_2$ was prepared as follows.

A mixed solution (E) was obtained by charging 824.9 g of ammonium heptamolybdate [$(NH_4)_6Mo_7O_{24} \cdot 4H_2O$], 135.8 g of ammonium metavanadate [$NH_4VO_3$], 176.7 g of antimony trioxide [$Sb_2O_3$] and 4.1 g of cerium(III) nitrate hexahydrate [$Ce(NO_3)_3 \cdot 6H_2O$] into 4,800 g of water, and heating the resultant mixture for 1 hour at 90° C. while stirring.

205.2 g of hydrogen peroxide solution containing 30 mass % as $H_2O_2$ was slowly charged into 627.0 g of the niobium mixed solution ($A_0$) while stirring under ice cooling. The resultant solution was then stirred and mixed to obtain a mixed solution (F).

Further, 390.0 g of silica powder having an average primary particle size of 12 nm was charged into 4,800 g of water, and the resultant mixture was stirred for 3 hours at room temperature to obtain a silica powder suspension (G).

The mixed solution (E) was cooled to 70° C., and then 3,226.6 g of the silica sol solution was added thereto. This silica sol solution was prepared in the same manner as in Example 1, and contained 40.7 mass % of $SiO_2$ and 10 wt ppm of nitrate ions in the silica sol. The nitrate ions in the silica sol were 27 wt ppm based on the $SiO_2$ in the silica sol. Consequently, the total mass of all the nitrate ions based on the $SiO_2$ derived from the silica sol in the slurry was 1,972 wt ppm. Further, 240.2 g of hydrogen peroxide solution containing 30 mass % as $H_2O_2$ was added, and the resultant mixture was stirred and mixed for 30 minutes at 50° C. Next, the mixed solution (F) and the above silica powder suspension (G) were added. The resultant mixture was stirred and mixed for 3 hours to obtain a raw material mixture solution.

A silica-supported catalyst was obtained by carrying out a drying step and a calcination step in the same manner as in Example 1 on the obtained raw material mixture solution. Using the obtained catalyst, a propane ammoxidation reaction and measurement of the degree of attrition of the catalyst were carried out according to the same manner as in Example 1. The results are shown in Table 1.

Example 10

A silica-supported catalyst represented by a charge composition formula of $Mo_1V_{0.25}Te_{0.20}Nb_{0.08}O_n$/40 mass %-$SiO_2$ was prepared as follows.

A mixed solution (H) was obtained by charging 1,237.4 g of ammonium heptamolybdate $[(NH_4)_6Mo_7O_{24}\cdot4H_2O]$, 203.6 g of ammonium metavanadate $[NH_4VO_3]$, and 319.7 g of telluric acid $[H_6TeO_6]$ into 6,500 g of water, and heating the resultant mixture for 1 hour at 90° C. while stirring.

200.5 g of hydrogen peroxide solution containing 30 mass % as $H_2O_2$ was slowly charged into 940.4 g of the niobium mixed solution $(A_0)$ while stirring under ice cooling. The resultant solution was then stirred and mixed to obtain a mixed solution $(A_1)$.

Further, 258 g of silica powder having an average primary particle size of 12 nm was charged into 3,460 g of water, and the resultant mixture was stirred for 3 hours at room temperature to obtain a silica powder suspension (D).

A silica sol, which is the carrier raw material, was prepared in the same manner as in Example 1. In the prepared silica sol, $SiO_2$ was 29.6 mass %. Nitric acid was added with a dropper so that the nitrate ions in the silica sol were 3 ppm. The nitrate ions in this silica sol were 10 wt ppm based on the $SiO_2$ in the silica sol.

The mixed solution (H) was cooled to 70° C., and then 2,180.7 g of the above-described silica sol was added thereto. Further, 240.2 g of hydrogen peroxide solution containing 30 mass % as $H_2O_2$ was added, and the resultant mixture was stirred and mixed for 30 minutes at 50° C. Next, the mixed solution $(A_1)$ and the above silica powder suspension (D) were added. The resultant mixture was stirred and mixed for 3 hours to obtain a raw material mixture solution.

A silica-supported catalyst was obtained by carrying out a drying step and a calcination step in the same manner as in Example 1 on the obtained raw material mixture solution. Using the catalyst, a propane ammoxidation reaction and measurement of the degree of attrition of the catalyst were carried out according to the same manner as in Example 1. The results are shown in Table 1.

Example 11

A silica-supported catalyst represented by a charge composition formula of $Mo_1V_{0.25}Te_{0.20}Nb_{0.08}Ce_{0.002}O_n$/40 mass %-$SiO_2$ was prepared as follows.

A mixed solution (H) was obtained by charging 1,237.4 g of ammonium heptamolybdate $[(NH_4)_6Mo_7O_{24}\cdot4H_2O]$, 203.6 g of ammonium metavanadate $[NH_4VO_3]$, 319.7 g of telluric acid $[H_6TeO_6]$ and 6.2 g of cerium(III) nitrate hexahydrate $[Ce(NO_3)_3\cdot6H_2O]$ into 6,500 g of water, and heating the resultant mixture for 1 hour at 90° C. while stirring.

200.5 g of hydrogen peroxide solution containing 30 mass % as $H_2O_2$ was slowly charged into 940.4 g of the niobium mixed solution $(A_0)$ while stirring under ice cooling. The resultant solution was then stirred and mixed to obtain a mixed solution $(A_1)$.

Further, 258 g of silica powder having an average primary particle size of 12 nm was charged into 3,460 g of water, and the resultant mixture was stirred for 3 hours at room temperature to obtain a silica powder suspension (D).

A silica sol, which is the carrier raw material, was prepared in the same manner as in Example 1. In the prepared silica sol, $SiO_2$ was 29.6 mass %. Nitric acid was added with a dropper so that the nitrate ions in the silica sol were 3 ppm. The nitrate ions in this silica sol were 10 wt ppm based on the $SiO_2$ in the silica sol.

The mixed solution (H) was cooled to 70° C., and then 2,180.7 g of the above-described silica sol was added thereto. Consequently, the total mass of all the nitrate ions based on the $SiO_2$ derived from the silica sol in the obtained slurry was 4,131 wt ppm. Further, 240.2 g of hydrogen peroxide solution containing 30 mass % as $H_2O_2$ was added, and the resultant mixture was stirred and mixed for 30 minutes at 50° C. Next, the mixed solution $(A_1)$ and the above silica powder suspension (D) were added. The resultant mixture was stirred and mixed for 3 hours to obtain a raw material mixture solution.

Using the obtained raw material mixture solution, a silica-supported catalyst was obtained by carrying out a drying step and a calcination step in the same method as in Example 1.

Using the obtained catalyst, a propane ammoxidation reaction and measurement of the degree of attrition of the catalyst were carried out according to the same method as in Example 1. The results are shown in Table 1.

Example 12

A silica-supported catalyst represented by a charge composition formula of $Mo_1V_{0.25}Sb_{0.26}Nb_{0.08}Ce_{0.002}W_{0.03}O_n$/40 mass %-$SiO_2$ was prepared as follows.

A mixed solution $(C_1)$ was obtained by charging 1,183.4 g of ammonium heptamolybdate $[(NH_4)_6Mo_7O_{24}\cdot4H_2O]$, 194.7 g of ammonium metavanadate $[NH_4VO_3]$, 253.0 g of antimony trioxide $[Sb_2O_3]$ and 5.9 g of cerium(III) nitrate hexahydrate $[Ce(NO_3)_3\cdot6H_2O]$ into 6,182 g of water, and heating the resultant mixture for 1 hour at 90° C. while stirring.

200.5 g of hydrogen peroxide solution containing 30 mass % as $H_2O_2$ was slowly charged into 940.4 g of the niobium mixed solution $(A_0)$ while stirring under ice cooling. The resultant solution was then stirred and mixed to obtain a mixed solution $(A_1)$.

Further, 258 g of silica powder having an average primary particle size of 12 nm was charged into 3,460 g of water, and the resultant mixture was stirred for 3 hours at room temperature to obtain a silica powder suspension (D).

A silica sol, which is the carrier raw material, was prepared in the same manner as in Example 1. In the prepared silica sol, $SiO_2$ was 29.6 mass %. Nitric acid was added with a dropper so that the nitrate ions in the silica sol were 34 ppm. The nitrate ions in this silica sol were 115 wt ppm based on the $SiO_2$ in the silica sol.

The obtained mixed solution ($C_1$) was cooled to 70° C., and then 2,180.7 g of the above-described silica sol was added thereto. Consequently, the total mass of all the nitrate ions based on the $SiO_2$ derived from the silica sol in the obtained slurry was 3,930 wt ppm. Further, 240.2 g of hydrogen peroxide solution containing 30 mass % as $H_2O_2$ was added, and the resultant mixture was stirred and mixed for 30 minutes at 50° C. Next, the mixed solution ($A_1$), 92 g of about 50 mass % ammonium metatungstate (($NH_4)_6[H_2W_{12}O_{40}]$aq) and the above silica powder suspension (D) were added. The resultant mixture was stirred and mixed for 3 hours to obtain a raw material mixture solution.

Using the obtained raw material mixture solution, a silica-supported catalyst was obtained by carrying out a drying step and a calcination step in the same method as in Example 1.

Using the obtained catalyst, a propane ammoxidation reaction and measurement of the degree of attrition of the catalyst were carried out according to the same method as in Example 1. The results are shown in Table 1.

Example 13

A silica-supported catalyst represented by a charge composition formula of $Mo_1V_{0.25}Sb_{0.26}Nb_{0.08}Ce_{0.002}Mn_{0.002}O_n$/40 mass %-$SiO_2$ was prepared as follows.

A mixed solution ($C_1$) was obtained by charging 1,183.2 g of ammonium heptamolybdate [$(NH_4)_6Mo_7O_{24}.4H_2O$], 194.7 g of ammonium metavanadate [$NH_4VO_3$], 253.4 g of antimony trioxide [$Sb_2O_3$] and 5.9 g of cerium(III) nitrate hexahydrate [$Ce(NO_3)_3.6H_2O$] into 6,182 g of water, and heating the resultant mixture for 1 hour at 90° C. while stirring.

192.0 g of hydrogen peroxide solution containing 30 mass % as $H_2O_2$ was slowly charged into 900.4 g of the niobium mixed solution ($A_0$) while stirring under ice cooling. The resultant solution was then stirred and mixed to obtain a mixed solution ($A_1$).

Further, 249 g of silica powder having an average primary particle size of 12 nm was charged into 3,360 g of water, and the resultant mixture was stirred for 3 hours at room temperature to obtain a silica powder suspension (D).

A silica sol, which is the carrier raw material, was prepared in the same manner as in Example 1. In the prepared silica sol, $SiO_2$ was 29.6 mass %. Nitric acid was added with a dropper and the like so that the nitrate ions in the silica sol were 34 ppm. The nitrate ions in this silica sol were 115 wt ppm based on the $SiO_2$ in the silica sol.

The mixed solution ($C_1$) was cooled to 70° C., and then 2,083.7 g of the above-described silica sol was added thereto. Further, 240.2 g of hydrogen peroxide solution containing 30 mass % as $H_2O_2$ was added, and the resultant mixture was stirred and mixed for 30 minutes at 50° C. Next, the mixed solution ($A_1$), 3.8 g of manganese nitrate hexahydrate [$Mn(NO_3)_2.6H_2O$] and the above silica powder suspension (D) were added. The resultant mixture was stirred and mixed for 3 hours to obtain a raw material mixture solution. Consequently, the total mass of all the nitrate ions based on the $SiO_2$ derived from the silica sol in the obtained slurry was 6,774 wt ppm.

Using the obtained raw material mixture solution, a silica-supported catalyst was obtained by carrying out a drying step and a calcination step in the same method as in Example 1.

Using the obtained catalyst, a propane ammoxidation reaction and measurement of the degree of attrition of the catalyst were carried out according to the same method as in Example 1. The results are shown in Table 1.

Comparative Example 1

A catalyst was prepared according to the same method as in Example 2, except that in the raw material mixture solution preparation step: nitric acid was not added to a silica sol prepared in the same manner as in Example 1 ($SiO_2$ concentration, 29.6 mass %); and cerium(III) carbonate and cerium (III) nitrate hexahydrate were used as the cerium raw material. The total mass of all the nitrate ions based on the $SiO_2$ derived from the silica sol in the obtained slurry was 186 wt ppm. (Prepared by undergoing the same steps as in Example 1.) The total mass of all the nitrate ions based on the $SiO_2$ derived from the silica sol in the obtained slurry was 186 wt ppm (prepared by undergoing the same steps as in Example 1).

Using the obtained catalyst, a propane ammoxidation reaction and measurement of the degree of attrition of the catalyst were carried out according to the same method as in Example 1. As a result, compared with Examples 1 to 10, the decrease in the yield of acrylonitrile is small whereas the degree of attrition was 1.0 mass %, which was extremely low. The results are shown in Table 1.

Comparative Example 2

A catalyst was prepared according to the same method as in Example 2, except that in the raw material mixture solution preparation step, a silica sol containing 29.6 mass % of $SiO_2$ and 2 wt ppm of nitrate ions in the silica sol (prepared in the same manner as in Example 1) was used. In addition, the mass of the nitrate ions in the silica sol with respect to the $SiO_2$ mass was 7 wt ppm. Consequently, the total mass of all the nitrate ions based on the $SiO_2$ derived from the silica sol in the obtained slurry was 4,133 wt ppm.

Using the obtained catalyst, a propane ammoxidation reaction and measurement of the degree of attrition of the catalyst were carried out according to the same method as in Example 1. As a result, compared with Examples 1 to 10, the decrease in the yield of acrylonitrile is small whereas the degree of attrition was as low as 0.9 mass %.

Comparative Example 3

A catalyst was prepared according to the same method as in Example 2, except that in the raw material mixture solution preparation step, a silica sol containing 29.6 mass % of $SiO_2$ and 88 wt ppm of nitrate ions in the silica sol solution (prepared in the same manner as in Example 1) was used. In addition, the mass of the nitrate ions in the silica sol with respect to the $SiO_2$ mass was 297 wt ppm. Consequently, the total mass of all the nitrate ions based on the $SiO_2$ derived from the silica sol in the obtained slurry was 4,424 wt ppm.

Using the obtained catalyst, a propane ammoxidation reaction and measurement of the degree of attrition of the catalyst were carried out according to the same method as in Example 1. As a result, compared with Examples 1 to 10, the yield of acrylonitrile was low. The results are shown in Table 1.

Comparative Example 4

A catalyst was prepared according to the same method as in Example 2, except that in the raw material mixture solution preparation step, a silica sol containing 29.6 mass % of $SiO_2$ and 110 wt ppm of nitrate ions in the silica sol (prepared in the same manner as in Example 1) was used. In addition, the mass of the nitrate ions in the silica sol with respect to the $SiO_2$ mass was 372 wt ppm. Consequently, the total mass of all the nitrate ions based on the $SiO_2$ derived from the silica sol in the obtained slurry was 4,498 wt ppm.

Using the obtained catalyst, a propane ammoxidation reaction and measurement of the degree of attrition were carried out according to the same method as in Example 1. As a result, compared with Examples 1 to 10, the yield of acrylonitrile was low. The results are shown in Table 1.

Example 14

An oxidation reaction of propane was carried out using the catalyst obtained in Example 1. The reaction was carried out under the same conditions as in Example 1, except that the mixed gas was fed at a reaction temperature of 380° C. with a molar ratio for the reaction gas composition of propane:steam:oxygen:helium of 1:14:3:10. The acrylonitrile yield was 34.5%.

TABLE 1

|  | Nitrate ion content based on $SiO_2$ in silica sol (wtppm) | AN Yield (%) | Degree of attrition (%) |
|---|---|---|---|
| Example 1 | 10 | 51.6 | 0.6 |
| Example 2 | 10 | 51.5 | 0.4 |
| Example 3 | 34 | 52.0 | 0.4 |
| Example 4 | 34 | 52.0 | 0.4 |
| Example 5 | 101 | 52.2 | 0.3 |
| Example 6 | 199 | 51.8 | 0.2 |
| Example 7 | 267 | 51.5 | 0.3 |
| Example 8 | 25 | 52.0 | 0.6 |
| Example 9 | 27 | 52.5 | 0.5 |
| Example 10 | 10 | 52.0 | 0.6 |
| Example 11 | 10 | 53.0 | 0.4 |
| Example 12 | 115 | 52.5 | 0.3 |
| Example 13 | 115 | 52.1 | 0.5 |
| Comparative Example 1 | 0 | 51.1 | 1.0 |
| Comparative Example 2 | 7 | 51.5 | 0.9 |
| Comparative Example 3 | 297 | 49.5 | 0.2 |
| Comparative Example 4 | 372 | 48 | 0.3 |

It can be clearly seen from the results of Table 1 that the silica-supported catalysts obtained using a silica sol having a nitrate ion content adjusted to a specific range as a carrier raw material (Examples 1 to 13) had an excellent acrylonitrile yield, and also had excellent catalyst attrition resistance.

The present application is based on a Japanese patent application filed with the Japan Patent Office on Jan. 30, 2009 (Japanese Patent Application No. 2009-020066), which is hereby incorporated by reference herein in its entirety.

INDUSTRIAL APPLICABILITY

A silica-supported catalyst obtained by the production method according to the present embodiment can be industrially utilized as a catalyst used in a propane vapor phase catalytic oxidation reaction or vapor phase catalytic ammoxidation reaction.

The invention claimed is:

1. A method for producing a silica-supported catalyst comprising Mo, V, Nb, and a component X (Sb and/or Te) to be used in a vapor phase catalytic oxidation or ammoxidation of propane, comprising the steps of:
   (I) preparing a raw material mixture solution by mixing Mo, V, Nb, component X, a silica sol, and water;
   (II) drying the raw material mixture solution to obtain a dry powder; and
   (III) calcining the dry powder, wherein
   the silica sol contains 10 to 270 wt ppm of nitrate ions based on $SiO_2$, to obtain a silica-supported catalyst.

2. The method for producing the silica-supported catalyst according to claim 1, wherein the silica-supported catalyst is represented by the following general composition formula (1), $$Mo_1V_aX_bNb_cZ_dO_n \qquad (1)$$

(wherein X represents Sb and/or Te, Z represents at least one element selected from the group consisting of W, Ta, Ti, Mn, B, Bi, Y, and rare earth elements, a, b, c, d, and n represent an atomic ratio of the individual element to the element Mo, a, b, c, and d are $0.1 \leq a \leq 1$, $0.01 \leq b \leq 1$, $0.01 \leq c \leq 0.6$, and $0 \leq d \leq 1$, respectively, and n represents a number determined based on an oxidation state of component metals).

3. The method for producing the silica-supported catalyst according to claim 1 or 2, wherein the component X is Sb.

4. The method for producing the silica-supported catalyst according to claim 2, wherein the component Z is at least one element selected from the group consisting of W, Mn, and Ce.

5. The method for producing the silica-supported catalyst according to claim 1 or 2, wherein a silica content of the silica-supported catalyst is 35 to 70 mass % based on a total mass of the catalyst.

6. The method for producing the silica-supported catalyst according to claim 1 or 2, wherein the raw material mixture solution further comprises a silica powder.